US012642818B2

(12) United States Patent

Ichim et al.

(10) Patent No.: US 12,642,818 B2

(45) Date of Patent: Jun. 2, 2026

(54) INDUCING AND ACCELERATING POST-STROKE RECOVERY BY ADMINISTRATION OF AMNIOTIC FLUID DERIVED STEM CELLS

(71) Applicant: Creative Medical Technologies, Inc., Phoenix, AZ (US)

(72) Inventors: Thomas Ichim, San Diego, CA (US); Amit Patel, Salt Lake City, UT (US)

(73) Assignee: Creative Medical Technologies, Inc., Phoenix, AZ (US)

( * ) Notice: Subject to any disclaimer, the term of this patent is extended or adjusted under 35 U.S.C. 154(b) by 427 days.

(21) Appl. No.: 15/702,735

(22) Filed: Sep. 12, 2017

(65) Prior Publication Data

US 2018/0071342 A1 Mar. 15, 2018

Related U.S. Application Data

(60) Provisional application No. 62/393,608, filed on Sep. 12, 2016.

(51) Int. Cl.

| | |
|---|---|
| *A61K 35/50* | (2015.01) |
| *C12N 5/00* | (2006.01) |
| *C12N 5/073* | (2010.01) |
| *C12N 5/0775* | (2010.01) |

(52) U.S. Cl.

CPC ............ *A61K 35/50* (2013.01); *C12N 5/0605* (2013.01); *C12N 5/0668* (2013.01); *C12N 2510/00* (2013.01)

(58) Field of Classification Search

CPC .............................. A61K 35/50; C12N 5/0668

See application file for complete search history.

(56) References Cited

U.S. PATENT DOCUMENTS

| | | | | |
|---|---|---|---|---|
| 7,569,385 | B2 * | 8/2009 | Haas ........................ | C12N 5/00 435/325 |
| 2014/0056842 | A1 * | 2/2014 | Sackner-Bernstein et al. ............ | A61K 38/193 424/85.1 |
| 2014/0127171 | A1 * | 5/2014 | Nocera et al. ......... | A61K 35/50 424/93.7 |

OTHER PUBLICATIONS

Rehni et al. "Amniotic fluid derived stem cells ameliorate focal cerebral ischaemia-reperfusion injury induced behavioural deficits in mice", Behavioural Brain Research 183 (2007) 95-100. (Year: 2007).*

Castillo-Melendez et al. "Stem cell therapy to protect and repair the developing brain: a review of mechanisms of action of cord blood and amnion epithelial derived cells", Frontiers in Neuroscience, Oct. 2013, vol. 7, Article 194, pp. 1-14. (Year: 2013).*

Liu et al. "Umbilical Cord-Derived Mesenchymal Stem Cells With Forced Expression of Hepatocyte Growth Factor Enhance Remyelination and Functional Recovery in a Rat Intracerebral Hemorrhage Model", Neurosurgery 67:357-366, 2010. (Year: 2010).*

Manuelpillai et al. "Amniotic membrane and amniotic cells: Potential therapeutic tools to combat tissue inflammation and fibrosis?", Placenta 32 (2011) S320-S325. (Year: 2011).*

Ming-Zhu et al. "Novel therapeutic strategy for stroke in rats by bone marrow stromal cells and ex vivo HGF gene transfer with HSV-1 vector" Journal of Cerebral Blood Flow & Metabolism (2006) 26, 1176-1188. (Year: 2006).*

Przybylski et al. "A review of the current research on the role of bFGF and VEGF in angiogenesis", Journal of Wound Care, vol. 18, No. 12 (2009). (Year: 2009).*

Jang et al. "Functional neural differentiation of human adipose tissue-derived stem cells using bFGF and forskolin", BMC Cell Biology, 11, 25 (2010). (Year: 2010).*

Kim et al, "Mammalian cell transfection: the present and the future" Anal Bioanal Chem. Aug. 2010; 397(8): 3173-3178. (Year: 2010).*

ThermoFisher Scientific, "Introduction to Transfection", Web page, 3 pages, accessed Dec. 1, 2020, retrieved from https://www.thermofisher.com/us/en/home/references/gibco-cell-culture-basics/transfection-basics/introduction-to-transfection.html. (Year: 2020).*

Myers et al. "Mesenchymal stem cells at the intersection of cell and gene therapy", Expert Opin. Biol. Ther. (2010) 10(12):1663-1679. (Year: 2010).*

Hanabusa et al. "Adrenomedullin Enhances Therapeutic Potency of Mesenchymal Stem Cells After Experimental Stroke in Rats" Stroke 2005;36:853-858. (Year: 2005).*

Jo et al. "Transplantation of Genetically Engineered Mesenchymal Stem Cells Improves Cardiac Function in Rats with Myocardial Infarction: Benefit of a Novel Nonviral Vector, Cationized Dextran" Tissue Engineering, vol. 13, No. 2, 2007, pp. 313-322. (Year: 2007).*

Futami et al. "Intracellular Delivery of Proteins into Mammalian Living Cells by Polyethylenimine-Cationization" Journal of Bioscience and Bioengineering (2005), vol. 99, No. 2, 95-103. (Year: 2005).*

"Transfection" Merriam-Webster.com Dictionary, Merriam-Webster, https://www.merriam-webster.com/dictionary/transfection, Accessed Jan. 19, 2023. (Year: 2023).*

* cited by examiner

*Primary Examiner* — James D Schultz

*Assistant Examiner* — James Joseph Graber

(74) *Attorney, Agent, or Firm* — Baumgartner Patent Law; Marc Baumgartner

(57) ABSTRACT

Disclosed are means of inducing and accelerating neurological recovery subsequent to a stroke through administration of amniotic fluid derived stem cells. In one embodiment stem cells are isolated from amniotic fluid and expanded under conditions allowing for expression of SSEA3, SSEA4, Tra1-60, Tra1-81, Tra2-54, Oct-4 and CD105. Said cells are subsequently administered into a patient having undergone a stroke, so as to induce direct regeneration (through transdifferentiation and replacement of neural tissue), as well as indirect regeneration (through production of growth factors that augment endogenous regenerative mechanisms while inhibiting degenerative mechanisms). In some embodiments factors produced by said amniotic fluid stem cells may be utilized instead of cells themselves. Said factors may include proteins, peptides, conditioned media, exosomes, or microvesicles.

17 Claims, No Drawings

INDUCING AND ACCELERATING POST-STROKE RECOVERY BY ADMINISTRATION OF AMNIOTIC FLUID DERIVED STEM CELLS

CROSS-REFERENCE TO RELATED APPLICATIONS

This application claims the benefit of priority to U.S. Provisional Application No. 62/393,608, filed Sep. 12, 2016, which is incorporated herein by reference in its entirety

FIELD OF THE INVENTION

The invention pertains to the field of tissue regeneration, more specifically, the invention pertains to regeneration of neural tissue after an ischemic insult, more specifically, the invention teaches the use of amniotic fluid derived cells in the induction and acceleration of post-stroke recovery.

BACKGROUND

Various insults to the brain of ischemic nature are associated with an initial loss of tissue due to immediate death, however a "stunned" are of neural tissue is susceptible to recovery. This temporarily dysfunctional tissue is termed the "penumbra". Furthermore areas of the brain have been demonstrated to possess regenerative activity after insult, however factors secreted by the insult prevent regeneration [1]. The pathogenesis of ischemic induced neurocognitive deficits involves apoptosis of neuroproliferative cells in the subgranular zone of the hippocampus, a region in the brain vital for learning and memory [2, 3]. Several studies have demonstrated a steep, long-term decline in subgranular neurogenesis in the dentate gyrus following ischemic damage [4] and direct irradiation of the hippocampus has been shown to result in pronounced cognitive deficits [5]. The cognitive deficits following various types of ischemia include deficits of learning, memory, and ability for spatial processing [6]. To date, no medication has been approved for induction and/or acceleration of post-ischemic brain insult recovery.

SUMMARY

Various aspects of the invention relating to the above are enumerated in the following paragraphs:

Aspect 1: A method of accelerating recovery subsequent to a brain injury associated with a loss of oxygen perfusion comprising the steps of: a) obtaining amniotic fluid; b) extracting from said amniotic fluid a population of cells with regenerative activity; c) expanding said amniotic fluid cells with regenerative activity in a manner to allow for increased number of cells while maintaining said regenerative activity; d) administering said expanded amniotic fluid derived cells with regenerative activity into a patient in need of treatment.

Aspect 2: The method of aspect 1, wherein said amniotic fluid is obtained from amniocentesis.

Aspect 3: The method of aspect 1, wherein said amniotic fluid is obtained from amniotic membranes.

Aspect 4: The method of aspect 1, wherein said loss of oxygen perfusion is caused by a stroke.

Aspect 5: The method of aspect 4, wherein said stroke is an ischemic stroke.

Aspect 6: The method of aspect 4, wherein said stroke is a hemorrhagic stroke.

Aspect 7: The method of aspect 4, wherein said stroke is a transient ischemic attack.

Aspect 8: The method of aspect 1, wherein said loss of oxygen perfusion is a traumatic brain injury.

Aspect 9: The method of aspect 8, wherein said traumatic brain injury is chronic traumatic encephalopathy.

Aspect 10: The method of aspect 1, wherein said loss of oxygen perfusion is caused by vascular disease of the brain.

Aspect 11: The method of aspect 1, wherein said loss of oxygen perfusion is result of global cerebral ischemia.

Aspect 12: The method of aspect 11, wherein said global cerebral ischemia occurs as a neonate.

Aspect 13: The method of aspect 12, wherein said neonatal global cerebral ischemia results in cerebral palsy.

Aspect 14: The method of aspect 12, wherein said global cerebral ischemic occurs due to asphyxiation.

Aspect 15: The method of aspect 12, wherein said global cerebral ischemic occurs due to drowning.

Aspect 16: The method of aspect 12, wherein said global cerebral ischemic occurs due to a cardiac event.

Aspect 17: The method of aspect 1, wherein said amniotic cells with regenerative activity are amniotic fluid stem cells.

Aspect 18: The method of aspect 1, wherein said amniotic cells with regenerative activity are amniotic fluid mesenchymal stem cells.

Aspect 19: The method of aspect 1, wherein said amniotic cells with regenerative activity possess an epitheliod morphology.

Aspect 20: The method of aspect 1, wherein said amniotic cells with regenerative activity possess expression of the markers SSEA3, SSEA4, Tra1-60, Tra1-81, Tra2-54, Oct-4 and CD105.

Aspect 21: The method of aspect 20, wherein said amniotic fluid cells are capable of differentiating into bone, cartilage and adipose tissue.

Aspect 22: The method of aspect 20, wherein said amniotic fluid cells possess less than 5% expression of SSEA1.

Aspect 23: The method of aspect 20, wherein said amniotic fluid cells are characterized by senescence after about 60 population doubling.

Aspect 24: The method of aspect 20, wherein said amniotic fluid cells are characterized by senescence after about 300 population doubling.

Aspect 25: The method of aspect 20, wherein said amniotic fluid cells are derived from a mammal.

Aspect 26: The method of aspect 20, wherein said mammal possesses a hemochorial placenta.

Aspect 27: The method of aspect 20, wherein said mammal is a human.

Aspect 28: The method of aspect 1, wherein said amniotic fluid is extracted in the first trimester.

Aspect 29: The method of aspect 1, wherein said amniotic fluid is extracted in the second trimester.

Aspect 30: The method of aspect 1, wherein said amniotic fluid is extracted in the third trimester.

Aspect 31: The method of aspect 1, wherein said amniotic fluid cells express one or more markers selected from a group comprising of: HLA class I, CD13, CD44, and CD49b.

Aspect 32: The method of aspect 1, wherein said amniotic fluid cells with regenerative activity are generated by the steps comprising of: a) harvesting amniotic fluid; b) centrifuging the amniotic fluid; c) plating cells onto plates coated with fibronectin in medium with 2% serum; d) selecting colonies which adhere to the plates; and e) isolating mortal, epithelioid morphology cells.

Aspect 33: The method of aspect 1, wherein said amniotic fluid derived cells with regenerative potential possess ability to inhibit secretion of inflammatory cytokines.

Aspect 34: The method of aspect 33, wherein said inflammatory cytokines are selected from a group comprising of; a) IFN-gamma; b) TNF-alpha; c) IL-2; d) IL-7; e) IL-12; f) IL-15; g) IL-17; h) IL-18; i) IL-21; j) IL-23; k) IL-27; l) IL-33; m) HMGB-1; and n) TRAIL.

Aspect 35: The method of aspect 1, wherein said amniotic fluid derived cells with regenerative potential are engineered for enhanced vivo persistence through transfection of a therapeutic peptide sequence encoding an anti-apoptotic gene.

Aspect 36: The method of aspect 35, wherein said enhancement of in vivo persistence is accomplished by enhancing the anti-thrombogenic properties of said amniotic fluid cells.

Aspect 37: The method of aspect 36, wherein said anti-thrombogenic properties are enhanced by inhibiting expression or function of thrombogenic molecules on said amniotic fluid cells.

Aspect 38: The method of aspect 36, wherein said amniotic fluid stem cells are engineered to express anti-thrombin III.

Aspect 39: The method of aspect 35, wherein said enhanced in vivo persistence is accomplished by modifying said amniotic fluid cells to avoid complement mediated lysis.

Aspect 40: The method of aspect 35, wherein said enhanced in vivo persistence is accomplished by modifying said amniotic fluid cells to avoid immune system killing.

Aspect 41: The method of aspect 39, wherein avoidance of complement mediated lysis is accomplished by expression of Decay Accelerating Factor (DAF) protein.

Aspect 42: The method of aspect 40, wherein said avoidance of immune system killing is accomplished by transfection with a molecule that blocks expression of HLA I and/or HLA II.

Aspect 43: The method of aspect 42, wherein said molecule is a siRNA selectively targeting transcripts associated with HLA I and/or HLA II.

Aspect 44: The method of aspect 42, wherein said molecule is a shRNA selectively targeting transcripts associated with HLA I and/or HLA II.

Aspect 45: The method of aspect 42, wherein said molecule is a ribozyme selectively targeting transcripts associated with HLA I and/or HLA II.

Aspect 46: The method of aspect 42, wherein said molecule is an antisense oligonucleotide selectively targeting transcripts associated with HLA I and/or HLA II.

Aspect 47: The method of aspect 40, wherein said avoidance of immune response is accomplished by transfection with an immune suppressive gene or plurality of genes.

Aspect 48: The method of aspect 47, wherein said immune suppressive gene is IL-10.

Aspect 49: The method of aspect 47, wherein said immune suppressive gene is IL-20.

Aspect 50: The method of aspect 47, wherein said immune suppressive gene is TGF-beta.

Aspect 51: The method of aspect 47, wherein said immune suppressive gene is HLA-G.

Aspect 52: The method of aspect 47, wherein said immune suppressive gene is indolamine 2,3 deoxygenase.

Aspect 53: The method of aspect 47, wherein said immune suppressive gene is arginase.

Aspect 54: The method of aspect 47, wherein said immune suppressive gene is IL-4.

Aspect 55: The method of aspect 47, wherein said immune suppressive gene is galectin.

Aspect 56: The method of aspect 47, wherein said immune suppressive gene is Fas ligand.

Aspect 57: The method of aspect 47, wherein said immune suppressive gene is PGE-2.

Aspect 58: The method of aspect 35, wherein said anti-apoptotic gene is obestatin.

Aspect 59: The method of aspect 35, wherein said anti-apoptotic gene is XIAP.

Aspect 60: The method of aspect 35, wherein said anti-apoptotic gene is surviving.

Aspect 61: The method of aspect 35, wherein said anti-apoptotic gene is BCL-XL.

Aspect 62: The method of aspect 35, wherein said anti-apoptotic gene is GATA-4.

Aspect 63: The method of aspect 35, wherein said anti-apoptotic gene is IGF-1

Aspect 64: The method of aspect 35, wherein said anti-apoptotic gene is EGF.

Aspect 65: The method of aspect 35, wherein said anti-apoptotic gene is heme-oxygenase-1.

Aspect 66: The method of aspect 35, wherein said anti-apoptotic gene is NF-kB.

Aspect 67: The method of aspect 35, wherein said anti-apoptotic gene is akt.

Aspect 68: The method of aspect 35, wherein said anti-apoptotic gene is pi3-k.

Aspect 69: The method of aspect 35, wherein prevention of apoptosis is accomplished by silencing or inhibiting one or more apoptosis stimulating genes.

Aspect 70: The method of aspect 69, wherein said molecules associated with induction of apoptosis are selected from a group comprising of: Fas, FasL, CASP1 (ICE), CASP10 (MCH4), CASP14, CASP2, CASP3, CASP4, CASP5, CASP6, CASP7, CASP8, CASP9, CFLAR (CASPER), CRADD, PYCARD (TMS1/ASC), ABL1, AKT1, BAD, BAK1, BAX, BCL2L11, BCLAF1, BID, BIK, BNIP3, BNIP3L, CASP1 (ICE), CASP10 (MCH4), CASP14, CASP2, CASP4, CASP6, CASP8, CD70 (TNFSF7), CIDEB, CRADD, FADD, FASLG (TNFSF6), HRK, LTA (TNFB), NOD1 (CARD4), PYCARD (TMS1/ASC), RIPK2, TNF, TNFRSF10A, TNFRSF10B (DR5), TNFRSF25 (DR3), TNFRSF9, TNFSF10 (TRAIL), TNFSF8, TP53, TP53BP2, TRADD, TRAF2, TRAF3, and TRAF4.

Aspect 71: The method of aspect 1, wherein said amniotic fluid cells with regenerative activity are endowed with ability to differentiate into cells of the neuronal lineage at a specified time point associated with homing to neuronal tissue.

Aspect 72: The method of aspect 1, wherein said amniotic fluid cells are administered intravenously.

Aspect 73: The method of aspect 1, wherein said amniotic fluid cells are administered intrathecally.

Aspect 74: The method of aspect 1, wherein said amniotic fluid cells are administered intraventricularly.

Aspect 75: The method of aspect 1, wherein said amniotic fluid cells are administered stereotactically.

Aspect 76: The method of aspect 1, wherein said amniotic fluid cells are administered intranasally.

Aspect 77: The method of aspect 71, wherein differentiation into the neural lineage is accomplished by transfection of a therapeutic polypeptide sequence selected from a group of polypeptide sequences comprising of: ADCYAP1R1, ARTN, BDNF, CD40 (TNFRSF5), CNTF, CNTFR, CRHBP, CRHR1, CRHR2, FRS2, FRS3, FUS, GDNF, GFRA1, GFRA2, GFRA3, GMFB, GMFG, MAGED1, MT3, NF1, NGF, NGFR, NGFRAP1, NR1I2, NRG1, NRG2, NTF3, NTF4, NTRK1, NTRK2, PSPN, PTGER2, TFG, TRO, VGF.

Aspect 78: The method of aspect 77, wherein said polypeptide sequences are utilized to induce differentiation of endogenous neural progenitors as a result of paracrine or systemic effects of said mesenchymal stem cell expressing said polypeptide sequences.

Aspect 79: The method of aspect 1, wherein said amniotic fluid cells are modified to possess enhanced angiogenic activity, said angiogenic activity selectively associated with stimulation of non-malignant neural tissue regeneration, wherein said enhanced ability to stimulate angiogenesis is accomplished through transfection with an angiogenic polypeptide.

Aspect 80: The method of aspect 79, wherein said angiogenic polypeptide is selected from a group comprising of: activin A, adrenomedullin, aFGF, ALK1, ALK5, ANF, angiogenin, angiopoietin-1, angiopoietin-2, angiopoietin-3, angiopoietin-4, bFGF, B61, bFGF inducing activity, cadherins, CAM-RF, cGMP analogs, ChDI, CLAF, claudins, collagen, collagen receptors .alpha..sub.1.beta..sub.1 and .alpha..sub.2.beta..sub.1, connexins, Cox-2, ECDGF (endothelial cell-derived growth factor), ECG, ECI, EDM, EGF, EMAP, endoglin, endothelins, endostatin, endothelial cell growth inhibitor, endothelial cell-viability maintaining factor, endothelial differentiation shpingolipid G-protein coupled receptor-1 (EDG1), ephrins, Epo, HGF, TGF-beta, PD-ECGF, PDGF, IGF, IL8, growth hormone, fibrin fragment E, FGF-5, fibronectin and fibronectin receptor .alpha.5.beta.1, Factor X, HB-EGF, HBNF, HGF, HUAF, heart derived inhibitor of vascular cell proliferation, IL1, IGF-2 IFN-gamma, integrin receptors, K-FGF, LIF, leiomyoma-derived growth factor, MCP-1, macrophage-derived growth factor, monocyte-derived growth factor, MD-ECI, MECIF, MMP 2, MMP3, MMP9, urokiase plasminogen activator, neuropilin (NRP1, NRP2), neurothelin, nitric oxide donors, nitric oxide synthases (NOSs), notch, occludins, zona occludins, oncostatin M, PDGF, PDGF-B, PDGF receptors, PDGFR-.beta., PD-ECGF, PAI-2, PD-ECGF, PF4, P1GF, PKR1, PKR2, PPAR-gamma, PPAR-gamma ligands, phosphodiesterase, prolactin, prostacyclin, protein S, smooth muscle cell-derived growth factor, smooth muscle cell-derived migration factor, sphingosine-1-phosphate-1 (SIP1), Syk, SLP76, tachykinins, TGF-beta, Tie 1, Tie2, TGF-.beta., and TGF-.beta. receptors, TIMPs, TNF-alpha-transferrin, thrombospondin, urokinase, VEGF-A, VEGF-B, VEGF-C, VEGF-D, VEGF-E, VEGF, VEGF.sub.164, VEGI, EG-VEGF.

DESCRIPTION OF THE INVENTION

The invention teaches the use of cells derived from amniotic fluid for treatment of ischemic neurological conditions. The cells described in the invention are immortal in culture, maintain euploidy for >1 year in culture, share markers with human ES cells, and are capable of differentiating into all three germ layers of the developing embryo, Endoderm, Mesoderm and Ectoderm. In a preferred embodiment the regenerative amniotic fluid cells are found in the amnion harvested during the second trimester of human pregnancies. It is known that amniotic fluid contains multiple morphologically-distinguishable cell types, the majority of the cells are prone to senescence and are lost from cultures. In one embodiment, fibronectin coated plates and culture conditions described in patent U.S. Pat. No. 7,569, 385 are used to grow cells from amniotic fluid harvests from normal 16-18 week pregnancies. The cells of the invention are of fetal origin, and have a normal diploid karyotype. Growth of the amniotic fluid stem cells as described in the invention for use in neurological ischemic conditions results in cells that are multipotent, as several main cell types have been derived from them. As used herein, the term "multipotent" refers to the ability of amniotic fluid regenerative cells to differentiate into several main cell types. The MAFSC cells may also be propagated under specific conditions to become "pluripotent." The term "pluripotent stem cells" describes stem cells that are capable of differentiating into any type of body cell, when cultured under conditions that give rise to the particular cell type. The Amniotic fluid regenerative cells are preferably isolated from humans. However, the Amniotic fluid regenerative cells may be isolated in a similar manner from other species. Examples of species that may be used to derive the Amniotic fluid regenerative cells include but are not limited to mammals, humans, primates, dogs, cats, goats, elephants, endangered species, cattle, horses, pigs, mice, rabbits, and the like.

The amniotic fluid-derived cells and MAFSC can be recognized by their specific cell surface proteins or by the presence of specific cellular proteins. Typically, specific cell types have specific cell surface proteins. These surface proteins can be used as "markers" to determine or confirm specific cell types. Typically, these surface markers can be visualized using antibody-based technology or other detection methods. One method of characterizing cellular markers includes FACS analysis.

The surface markers of the isolated MAFSC cells derived from independently-harvested amniotic fluid samples were tested for a range of cell surface and other markers, using monoclonal antibodies and FACS analysis. These cells can be characterized by the following cell surface markers: SSEA3, SSEA4, Tra-1-60, Tra-1-81, Tra-2-54. The MAFSC cells can be distinguished from mouse ES cells in that the MAFSC cells do not express the cell surface marker SSEA1. Additionally, MAFSC express the stem cell transcription factor Oct-4. The MAFSC cells can be recognized by the presence of at least one, or at least two, or at least three, or at least four, or at least five, or at least six, or all of the following cellular markers SSEA3, SSEA4, Tra-1-60, Tra-1-81, Tra-2-54 and Oct-4.

In some embodiments of the present invention, the SSEA3 marker is expressed in a range of from about 90%, 92%, 94% to about 96%, 98%, 99%, or 100% of the cells in the MAFSC culture. The SSEA4 marker can be expressed, for example, in a range of from about 90%, 92%, 94% to about 96%, 98%, 99%, or 100% of the cells in the MAFSC culture. In some embodiments of the present invention, the Tra-1-60 marker expressed, for example, in a range of from about 60%, 65%, or 70% to about 85%, 90%, or 95% of the cells in the MAFSC culture. In some embodiments of the present invention, the Tra-1-81 marker is expressed in a range of from about 70%, 75%, or 80% to about 85%, 90%, or 95% of the cells in the MAFSC culture. The Tra-2-84 marker can be expressed, for example, in a range of from about 55%, 60%, 65%, or 70% to about 80%, 90%, or 95% of the cells in the MAFSC culture. In some embodiments of the present invention, the Oct-4 marker is expressed in a range of from about 25%, 30%, 35%, or 40% to about 45%, 55%, 65%, or 70% of the cells in the MAFSC culture.

The MAFSC cultures express very little or no SSEA-1 marker. In addition to the embryo stem cell markers SSEA3, SSEA4, Tra1-60, Tra1-81, Tra2-54, Oct-4 the amniotic fluid regenerative cells also expressed high levels of the cell surface antigens that are normally found on human mesenchymal stem cells, but not normally on human embryo stem cells (M F Pittinger et al., Science 284:143-147, 1999; S Gronthos et al., J. Cell Physiol. 189:54-63, 2001). This set of markers includes CD13 (99.6%) aminopeptidase N, CD44 (99.7%) hyaluronic acid-binding receptor, CD49b (99.8%) collagen/laminin-binding integrin alpha2, and CD105 (97%) endoglin. The presence of both the embryonic stem cell markers and the hMSC markers on the MAFSC cell cultures indicates that amniotic fluid-derived MAFSC cells, grown and propagated as described here, represent a novel class of human stem cells that combined the characteristics of hES cells and of hMSC cells.

In some embodiments of the invention, at least about 90%, 94%, 97%, 99%, or 100% of the cells in the culture express CD13. In additional embodiments, at least about 90%, 94%, 97%, 99%, or 100% of the cells in the culture express CD44. In some embodiments of the invention, a range from at least about 90%, 94%, 97%, 99%, 99.5%, or 100% of the cells in the culture express CD49b. In further embodiments of the invention, a range from at least about 90%, 94%, 97%, 99%, 99.5%, or 100% of the cells in the culture express CD105.

In a particularly advantageous embodiment, the amniotic fluid regenerative cells are human stem cells that can be propagated for an indefinite period of time in continuous culture in an undifferentiated state. The term "undifferentiated" refers to cells that have not become specialized cell types. A "nutrient medium" is a medium for culturing cells containing nutrients that promote proliferation. The nutrient medium may contain any of the following in an appropriate combination: isotonic saline, buffer, amino acids, antibiotics, serum or serum replacement, and exogenously added factors.

The cells may also be "banked" or stored in a manner that allows the cells to be revived as needed in the future, a An aliquot of the undifferentiated cells can be removed at any time, to be differentiated into a particular cell type or tissue type, and may then be used to treat a disease or to replace malfunctioning tissues in a patient. Since the cells are harvested from the amniotic fluid, the cells can be stored so that an individual can have access to his or her own undifferentiated cells for an entire lifetime.

The Amniotic fluid regenerative cells may be grown in an undifferentiated state for as long as desired (and optionally stored as described above), and can then be cultured under certain conditions to allow progression to a differentiated state. By "differentiation" is meant the process whereby an unspecialized cell acquires the features of a specialized cell such as a heart, liver, muscle, pancreas or other organ or tissue cell. The Amniotic fluid regenerative cells, when cultured under certain conditions, have the ability to differentiate in a regulated manner into three or more subphenotypes. Once sufficient cellular mass is achieved, cells can be differentiated into endodermal, mesodermal and ectodermal derived tissues in vitro and in vivo. This planned, specialized differentiation from undifferentiated cells towards a specific cell type or tissue type is termed "directed differentiation." Exemplary cell types that may be prepared from Amniotic fluid regenerative cells using directed differentiation include but are not limited to fat cells, cardiac muscle cells, epithelial cells, liver cells, brain cells, blood cells, neurons, glial cells, pancreatic cells, and the like.

General methods relating to stem cell differentiation techniques that may be useful for differentiating the Amniotic fluid regenerative cells of this invention can be found in general texts such as: Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998); and in Stem cell biology (L. M. Reid, Curr. Opinion Cell Biol. 2:121, 1990), each of which is incorporated by reference herein in its entirety.

Differentiation agents, maturation agents, or maturation factors may be useful to allow progression to certain cell types. Examples of differentiation agents, that may be used include but are not limited to agents, such as N-butyrate, which are useful for differentiating embryonic stem cells to liver cells are described in U.S. Pat. No. 6,506,574, to Rambhatla et al. Optionally, maturation agents, or maturation factors, such as, for example, growth factors, peptide hormones, cytokines, ligand receptor complexes, corticosteroids, retinoic acid, and even organic solvents like DMSO have been found to effect differentiation of embryonic stem cells (U.S. Pat. No. 6,506,574). Other suitable differentiating or maturation agents which may be used include but are not limited to a glucocorticoid with cAMP-elevating agents, methyl-isobutylxanthine, indomethacin, and the like.

The isolated Amniotic fluid regenerative cells or their derivatives may be used to treat diseases in humans or animals. As used herein the term "treat" or "treatment" refer to both therapeutic treatment and prophylactic or preventative measures, wherein the object is to prevent, slow down (lessen), or reverse an undesired physiological change or disorder. The term "treat" also refers to the characterization of the type or severity of disease which may have ramifications for future prognosis, or need for specific treatments. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

To treat a human or animal in need of treatment, the Amniotic fluid regenerative cells can be either regenerated into segments of a desired tissue, then transplanted into the patient, or can be regenerated into a whole tissue that will be used to replace the failing tissue, or can be injected into a tissue of interest as whole cells, where they will regenerate at the injected location.

In some embodiments of the invention amniotic fluid cells are transfected to possess enhanced neuromodulatory and neuroprotective properties. Said transfection may be accomplished by use of lentiviral vectors, said means to perform lentiviral mediated transfection are well-known in the art and discussed in the following references [7-13]. Some specific examples of lentiviral based transfection of genes into MSC include transfection of SDF-1 to promote stem cell homing, particularly hematopoietic stem cells [14], GDNF to treat Parkinson's in an animal model [15], HGF to accelerate remyelination in a brain injury model [16], NUR77 to enhance migration [17], BDNF to reduce ocular nerve damage in response to hypertension [18], HIF-1 alpha to stimulate osteogenesis [19], dominant negative CCL2 to reduce lung fibrosis [20], interferon beta to reduce tumor progression [21], HLA-G to enhance immune suppressive activity [22], cytosine deaminase [23], OCT-4 to reduce senescence [24, 25], BAMBI to reduce TGF expression and protumor effects [26], HO-1 for radioprotection [27], LIGHT to induce antitumor activity [28], miR-126 to enhance angiogenesis [29, 30], bc1-2 to induce generation of nucleus pulposus cells [31], telomerase to induce neurogenesis [32], CXCR4 to accelerate hematopoietic recovery [33] and reduce unwanted immunity [34], wnt11 to promote regenerative cytokine production [35], and the HGF antagonist NK4 to reduce cancer [36].

Cell cultures are tested for sterility weekly, endotoxin by limulus amebocyte lysate test, and mycoplasma by DNA-fluorochrome stain.

In one embodiment of the invention amniotic fluid stem cells are transfected with anti-apoptotic proteins to enhance in vivo longevity. The present invention includes a method of using amniotic fluid stem cells that have been cultured under conditions to express increased amounts of at least one anti-apoptotic protein as a therapy to inhibit or prevent apoptosis. In one embodiment, the amniotic fluid stem cells which are used as a therapy to inhibit or prevent apoptosis have been contacted with an apoptotic cell. The invention is based on the discovery that amniotic fluid stem cells that have been contacted with an apoptotic cell express high levels of anti-apoptotic molecules. In some instances, the amniotic fluid stem cells that have been contacted with an apoptotic cell secrete high levels of at least one anti-apoptotic protein, including but not limited to, STC-1, BCL-2, XIAP, Survivin, and Bcl-2XL. Methods of transfecting antiapoptotic genes into MSC have been previously described which can be applied to the current invention, said antiapoptotic genes that can be utilized for practice of the invention, in a nonlimiting way, include GATA-4 [37], FGF-2 [38], bcl-2 [31, 39], and HO-1 [40]. Based upon the disclosure provided herein, cells can be obtained from any source of amniotic. The cells may be autologous with respect to the recipient (obtained from the same host) or allogeneic with respect to the recipient. In addition, the cells may be xenogeneic to the recipient (obtained from an animal of a different species). In one embodiment of the invention MSC are pretreated with agents to induce expression of antiapoptotic genes, one example is pretreatment with exendin-4 as previously described [41].

REFERENCES

1. Jannoun, L. and H. J. Bloom, *Long-term psychological effects in children treated for intracranial tumors*. Int J Radiat Oncol Biol Phys, 1990. 18(4): p. 747-53.

2. Peissner, W., et al., *Ionizing radiation-induced apoptosis of proliferating stem cells in the dentate gyrus of the adult rat hippocampus*. Brain Res Mol Brain Res, 1999. 71(1): p. 61-8.

3. Pereira Dias, G., et al., *Consequences of cancer treatments on adult hippocampal neurogenesis: implications for cognitive function and depressive symptoms*. Neuro Oncol, 2014. 16(4): p. 476-92.

4. Mizumatsu, S., et al., *Extreme sensitivity of adult neurogenesis to low doses of X-irradiation*. Cancer Res, 2003. 63(14): p. 4021-7.

5. Abayomi, O. K., *Pathogenesis of cognitive decline following therapeutic irradiation for head and neck tumors*. Acta Oncol, 2002. 41(4): p. 346-51.

6. Roman, D. D. and P. W. Sperduto, *Neuropsychological effects of cranial radiation: current knowledge and future directions*. Int J Radiat Oncol Biol Phys, 1995. 31(4): p. 983-98.

7. Zhang, X. Y., et al., *Lentiviral vectors for sustained transgene expression in human bone marrow-derived stromal cells*. Mol Ther, 2002. 5(5 Pt 1): p. 555-65.

8. Kyriakou, C. A., et al., *Human mesenchymal stem cells (hMSCs) expressing truncated soluble vascular endothelial growth factor receptor (tsFlk-1) following lentiviral-mediated gene transfer inhibit growth of Burkitt's lymphoma in a murine model*. J Gene Med, 2006. 8(3): p. 253-64.

9. Worsham, D. N., et al., *In vivo gene transfer into adult stem cells in unconditioned mice by in situ delivery of a lentiviral vector*. Mol Ther, 2006. 14(4): p. 514-24.

10. Rabin, N., et al., *A new xenograft model of myeloma bone disease demonstrating the efficacy of human mesenchymal stem cells expressing osteoprotegerin by lentiviral gene transfer*. Leukemia, 2007. 21(10): p. 2181-91.

11. Kallifatidis, G., et al., *Improved lentiviral transduction of human mesenchymal stem cells for therapeutic intervention in pancreatic cancer*. Cancer Gene Ther, 2008. 15(4): p. 231-40.

12. Meyerrose, T. E., et al., *Lentiviral-transduced human mesenchymal stem cells persistently express therapeutic levels of enzyme in a xenotransplantation model of human disease*. Stem Cells, 2008. 26(7): p. 1713-22.

13. McGinley, L., et al., *Lentiviral vector mediated modification of mesenchymal stem cells & enhanced survival in an in vitro model of ischaemia*. Stem Cell Res Ther, 2011. 2(2): p. 12.

14. Liang, X., et al., *Human bone marrow mesenchymal stem cells expressing SDF-1 promote hematopoietic stem cell function of human mobilised peripheral blood CD34+ cells in vivo and in vitro*. Int J Radiat Biol, 2010. 86(3): p. 230-7.

15. Glavaski-Joksimovic, A., et al., *Glial cell line-derived neurotrophic factor-secreting genetically modified human bone marrow-derived mesenchymal stem cells promote recovery in a rat model of Parkinson's disease*. J Neurosci Res, 2010. 88(12): p. 2669-81.

16. Liu, A. M., et al., *Umbilical cord-derived mesenchymal stem cells with forced expression of hepatocyte growth factor enhance remyelination and functional recovery in a rat intracerebral hemorrhage model*. Neurosurgery, 2010. 67(2): p. 357-65; discussion 365-6.

17. Maijenburg, M. W., et al., *Nuclear receptors Nur77 and Nurr1 modulate mesenchymal stromal cell migration*. Stem Cells Dev, 2012. 21(2): p. 228-38.

18. Harper, M. M., et al., *Transplantation of BDNF-secreting mesenchymal stem cells provides neuroprotection in chronically hypertensive rat eyes*. Invest Ophthalmol Vis Sci, 2011. 52(7): p. 4506-15.

19. Zou, D., et al., *In vitro study of enhanced osteogenesis induced by HIF-1alpha-transduced bone marrow stem cells*. Cell Prolif, 2011. 44(3): p. 234-43.

20. Saito, S., et al., *Mesenchymal stem cells stably transduced with a dominant-negative inhibitor of CCL2 greatly attenuate bleomycin-induced lung damage*. Am J Pathol, 2011. 179(3): p. 1088-94.

21. Seo, K. W., et al., *Anti-tumor effects of canine adipose tissue-derived mesenchymal stromal cell-based interferon-beta gene therapy and cisplatin in a mouse melanoma model*. Cytotherapy, 2011. 13(8): p. 944-55.

22. Yang, H. M., et al., *Enhancement of the immunosuppressive effect of human adipose tissue-derived mesenchymal stromal cells through HLA-G1 expression.* Cytotherapy, 2012. 14(1): p. 70-9.

23. Fei, S., et al., *The antitumor effect of mesenchymal stem cells transduced with a lentiviral vector expressing cytosine deaminase in a rat glioma model.* J Cancer Res Clin Oncol, 2012. 138(2): p. 347-57.

24. Jaganathan, B. G. and D. Bonnet, *Human mesenchymal stromal cells senesce with exogenous OCT4.* Cytotherapy, 2012. 14(9): p. 1054-63.

25. Han, S. H., et al., *Effect of ectopic OCT4 expression on canine adipose tissue-derived mesenchymal stem cell proliferation.* Cell Biol Int, 2014. 38(10): p. 1163-73.

26. Shangguan, L., et al., *Inhibition of TGF-beta/Smad signaling by BAMBI blocks differentiation of human mesenchymal stem cells to carcinoma-associated fibroblasts and abolishes their protumor effects.* Stem Cells, 2012. 30(12): p. 2810-9.

27. Kearns-Jonker, M., et al., *Genetically Engineered Mesenchymal Stem Cells Influence Gene Expression in Donor Cardiomyocytes and the Recipient Heart.* J Stem Cell Res Ther, 2012. S1.

28. Ma, G. L., et al., [*Study of inhibiting and killing effects of transgenic LIGHT human umbilical cord blood mesenchymal stem cells on stomach cancer*]. Zhonghua Wei Chang Wai Ke Za Zhi, 2012. 15(11): p. 1178-81.

29. Huang, F., et al., *Mesenchymal stem cells modified with miR-126 release angiogenic factors and activate Notch ligand Delta-like-4, enhancing ischemic angiogenesis and cell survival.* Int J Mol Med, 2013. 31(2): p. 484-92.

30. Huang, F., et al., *Overexpression of miR-126 promotes the differentiation of mesenchymal stem cells toward endothelial cells via activation of PI3K/Akt and MAPK/ERK pathways and release of paracrine factors.* Biol Chem, 2013. 394(9): p. 1223-33.

31. Fang, Z., et al., *Differentiation of GFP-Bcl-2-engineered mesenchymal stem cells towards a nucleus pulposus-like phenotype under hypoxia in vitro.* Biochem Biophys Res Commun, 2013. 432(3): p. 444-50.

32. Madonna, R., et al., *Transplantation of mesenchymal cells rejuvenated by the overexpression of telomerase and myocardin promotes revascularization and tissue repair in a murine model of hindlimb ischemia.* Circ Res, 2013. 113(7): p. 902-14.

33. Zang, Y., et al., [*Influence of CXCR4 overexpressed mesenchymal stem cells on hematopoietic recovery of irradiated mice*]. Zhongguo Shi Yan Xue Ye Xue Za Zhi, 2013. 21(5): p. 1261-5.

34. Cao, Z., et al., *Protective effects of mesenchymal stem cells with CXCR4 up-regulation in a rat renal transplantation model.* PLoS One, 2013. 8(12): p. e82949.

35. Liu, S., et al., *Overexpression of Wnt11 promotes chondrogenic differentiation of bone marrow-derived mesenchymal stem cells in synergism with TGF-beta.* Mol Cell Biochem, 2014. 390(1-2): p. 123-31.

36. Zhu, Y., et al., *Mesenchymal stem cell-based NK4 gene therapy in nude mice bearing gastric cancer xenografts.* Drug Des Devel Ther, 2014. 8: p. 2449-62.

37. Yu, B., et al., *Enhanced mesenchymal stem cell survival induced by GATA-4 overexpression is partially mediated by regulation of the miR-15 family.* Int J Biochem Cell Biol, 2013. 45(12): p. 2724-35.

38. Xu, W., et al., *Basic fibroblast growth factor expression is implicated in mesenchymal stem cells response to light-induced retinal injury.* Cell Mol Neurobiol, 2013. 33(8): p. 1171-9.

39. Li, W., et al., *Bcl-2 engineered MSCs inhibited apoptosis and improved heart function.* Stem Cells, 2007. 25(8): p. 2118-27.

40. Tsubokawa, T., et al., *Impact of anti-apoptotic and anti-oxidative effects of bone marrow mesenchymal stem cells with transient overexpression of heme oxygenase-1 on myocardial ischemia.* Am J Physiol Heart Circ Physiol, 2010. 298(5): p. H1320-9.

41. Zhou, H., et al., *Exendin-4 protects adipose-derived mesenchymal stem cells from apoptosis induced by hydrogen peroxide through the PI3K/Akt-Sfrp2 pathways.* Free Radic Biol Med, 2014. 77: p. 363-75.

The invention claimed is:

1. A method of accelerating recovery subsequent to a brain injury associated with a loss of oxygen perfusion comprising the steps of:
   a) obtaining amniotic fluid;
   b) extracting from said amniotic fluid a population of cells with regenerative activity;
   c) expanding said amniotic fluid cells with regenerative activity in a manner to allow for increased number of cells while maintaining said regenerative activity;
   d) modifying said amniotic fluid cells to possess enhanced angiogenic activity associated with stimulation of non-malignant neural tissue regeneration, wherein said enhanced ability to stimulate angiogenesis is accomplished through transfecting adrenomedullin polypeptide into said amniotic fluid cells wherein no adrenomedullin encoding nucleic acid is transfected into said amniotic fluid cells; and
   e) administering said expanded and enhanced amniotic fluid derived cells with regenerative and enhanced angiogenic activity into a patient who has suffered from a brain injury,
   wherein said amniotic cells with regenerative activity are amniotic fluid stem cells.

2. The method of claim 1, wherein said amniotic fluid is obtained from amniocentesis.

3. The method of claim 1, wherein said amniotic fluid is obtained from amniotic membranes.

4. The method of claim 1, wherein said loss of oxygen perfusion is caused by a stroke.

5. The method of claim 4, wherein said stroke is an ischemic stroke.

6. The method of claim 4, wherein said stroke is a hemorrhagic stroke.

7. The method of claim 4, wherein said stroke is a transient ischemic attack.

8. The method of claim 1, wherein said loss of oxygen perfusion is a traumatic brain injury.

9. The method of claim 8, wherein said traumatic brain injury is chronic traumatic encephalopathy.

10. The method of claim 1, wherein said loss of oxygen perfusion is caused by vascular disease of the brain.

11. The method of claim 1, wherein said loss of oxygen perfusion is result of global cerebral ischemia.

12. The method of claim 11, wherein said global cerebral ischemia occurs as a neonate.

13. The method of claim 12, wherein said neonatal global cerebral ischemia results in cerebral palsy.

14. The method of claim 12, wherein said global cerebral ischemic occurs due to asphyxiation.

15. The method of claim 12, wherein said global cerebral ischemic occurs due to drowning.

16. The method of claim 12, wherein said global cerebral ischemic occurs due to a cardiac event.

17. The method of claim 1, wherein said amniotic cells with regenerative activity possess expression of the markers SSEA3, SSEA4, Tra1-60, Tra1-81, Tra2-54, Oct-4 and CD105.

* * * * *